(12) United States Patent
Salud et al.

(10) Patent No.: US 11,741,548 B1
(45) Date of Patent: Aug. 29, 2023

(54) METHODS AND APPARATUS TO ESTIMATE COSTS OF PRESCRIPTIONS

(71) Applicant: WALGREEN CO., Deerfield, IL (US)

(72) Inventors: Lawrence Salud, Chicago, IL (US); August Karlstedt, San Diego, CA (US)

(73) Assignee: WALGREEN CO., Deerfield, IL (US)

( * ) Notice: Subject to any disclaimer, the term of this patent is extended or adjusted under 35 U.S.C. 154(b) by 547 days.

(21) Appl. No.: 16/521,290

(22) Filed: Jul. 24, 2019

(51) Int. Cl.
*G06Q 40/08* (2012.01)
*G06N 20/00* (2019.01)
*G16H 20/10* (2018.01)

(52) U.S. Cl.
CPC ............ *G06Q 40/08* (2013.01); *G06N 20/00* (2019.01); *G16H 20/10* (2018.01)

(58) Field of Classification Search
CPC ......... G16H 50/30; G16H 50/20; G16H 10/60; G16H 30/40; G16H 40/20; G16H 50/50; G16H 10/20; G16H 20/30; G16H 15/00; G16H 40/63; G16H 40/67
See application file for complete search history.

(56) References Cited

U.S. PATENT DOCUMENTS

2015/0142479 A1* 5/2015 Porter et al. ....... G06Q 30/0283
705/4
2020/0273570 A1* 8/2020 Subramanian et al. G06N 7/005

FOREIGN PATENT DOCUMENTS

WO 2016161137 A1* 10/2016 ............ G06F 17/30289

OTHER PUBLICATIONS

Bertsimas, Dimitris, et al. "Algorithmic Prediction of Health-Care Costs." Operations Research 56.6 (2008): 1382-1392. (Year: 2008).*
Kelly et al., "The Last Mile: Operationalizing Data Science", Pivotal Software, Inc., 2017, https://content.pivotal.io/white-papers/the-last-mile-operationalizing-data-science, 12 pages.
Microsoft Docs, "Mining Structures (Analysis Services - Data Mining)", Microsoft, 2018, https://docs.microsoft.com/en-us/sql/analysis-services/data-mining/mining-structures-analysis-services-data-mining?view=sql-server-2017, as downloaded on Sep. 5, 2019, 8 pages.

* cited by examiner

*Primary Examiner* — Linh Giang Le
*Assistant Examiner* — Constantine Siozopoulos
(74) *Attorney, Agent, or Firm* — MARSHALL, GERSTEIN & BORUN LLP; Randall G. Rueth

(57) ABSTRACT

Example methods, apparatus, and articles of manufacture to estimate costs of prescriptions are disclosed herein. An example computer-implemented method, executed by a processor, to estimate a cost of a prescription for a medication includes receiving, with a processor, a prescription for a medication for a patient, receiving, with the processor from an entity, a request for an estimated cost for the prescription, processing, with a machine learning model, the prescription to determine the estimated cost of the medication for the patient, and providing, with the processor, the estimated cost to the entity.

24 Claims, 6 Drawing Sheets

METHODS AND APPARATUS TO ESTIMATE COSTS OF PRESCRIPTIONS

FIELD OF THE DISCLOSURE

This disclosure relates generally to prescriptions, and, more particularly, to estimate costs of prescriptions.

BACKGROUND

Prescribers (e.g., medical professionals) write prescriptions for medications for their patients. Pharmacies process a prescription for a patient by submitting the prescription to a payor, e.g., an insurance company, who indicates how much of the cost of the prescription will be covered by the patient's insurance. The difference is paid by the patient when the medication is picked up, mailed, etc.

Figure 1:
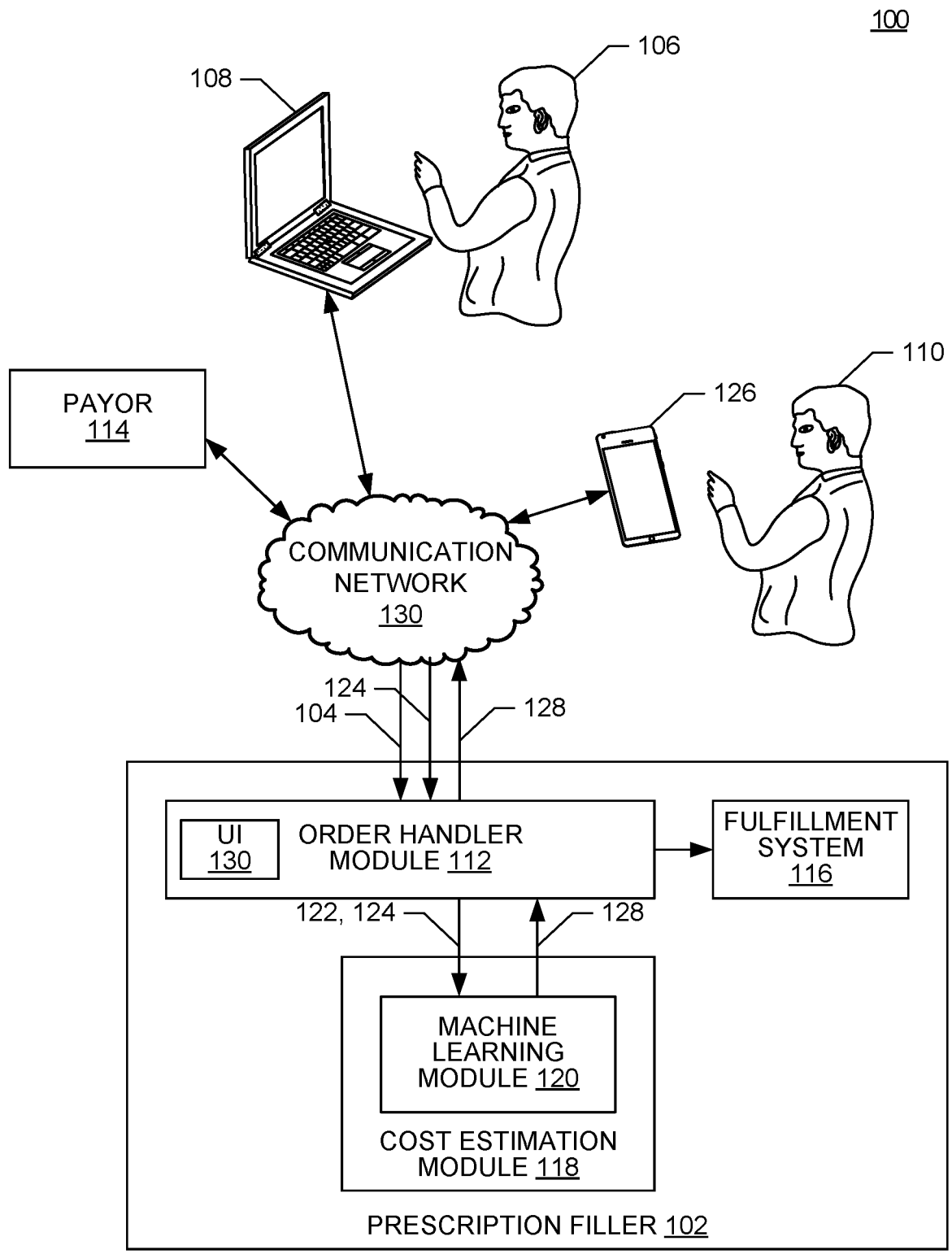
FIG. 1 is a block diagram of an example system to estimate costs of prescriptions, in accordance with teachings of this disclosure.

The figures depict embodiments of this disclosure for purposes of illustration only. One skilled in the art will readily recognize from the following discussion that alternate embodiments of the structures and methods illustrated herein may be employed without departing from the principles set forth herein.

In general, the same reference numbers will be used throughout the drawing(s) and accompanying written description to refer to the same or like parts. The figures are not to scale. Connecting lines or connectors shown in the various figures presented are intended to represent example functional relationships and/or physical or logical couplings between the various elements.

DETAILED DESCRIPTION

A large number (e.g., 10 percent) of prescriptions for medications are not picked up by patients. For example, a patient may find their prescription to be unaffordable or are unwilling to pay that much when they go to pick up their medication. When a prescription is not picked up, a return of the prescription has to be processed. The medication has to be returned to stock. If a payor (e.g., an insurance company, a manufacturer, etc.) has already paid for the prescription, a refund has to be issued. The costs and labor to return the prescription are in addition to the costs and labor to originally fill the prescription. Accordingly, prescriptions that are not picked up represent a financial overhead that impacts profitability. Additionally, prescriptions that are not picked up represent patients that are not receiving the medical care prescribed by their prescriber.

To overcome these and/or other problems, methods, apparatus, and articles of manufacture to estimate costs of prescriptions are disclosed herein. In disclosed examples, costs of prescriptions are estimated without submitting a claim or inquiry for the prescription to a payor entity or manufacturer. In disclosed examples, estimated costs of prescriptions are provided to patients and/or prescribers before they are filled. A patient is, thus, provided with additional information they may need to determine whether they will actually pick up their prescription. Further, if an estimated cost is provided to a patient while they are in a vicinity of their prescriber (e.g., with their doctor), the prescriber can select an alternative medication when the patient indicates the original medication would be too expensive. Thus, a prescriber can ensure their patient is properly treated at a cost that the patient can afford or is willing to pay. In examples disclosed herein, machine learning is used to estimate costs of prescriptions. While the examples disclosed herein are described with reference to medications, aspects of this disclosure can be used to estimate costs for other goods requiring a prescription (e.g., therapy, medical tests, medical procedures, medical supplies, etc.).

Reference will now be made in detail to non-limiting examples, some of which are illustrated in the accompanying drawings.

FIG. 1 is a diagram of an example system 100 to, among possibly other things, estimate costs of prescriptions for medications. The system 100 includes a prescription filler 102 (e.g., a pharmacy, etc.) to fill prescriptions 104 for medications. The prescriptions 104 may be received from any number or type(s) prescriber (e.g., a medical professional, a doctor, a nurse practitioner, a dentist, etc.) or representatives thereof, one of which is designated at reference numeral 106, via any number or type(s) of user devices (e.g., a facsimile, a laptop computer, a tablet, a smartphone, etc.), one of which is designated at reference numeral 108. While not shown in FIG. 1, prescriptions 104 may additionally, or alternatively, be physically mailed or faxed to, or physically dropped off at the prescription filler 102 by the prescriber 106 (or a representative thereof) or by a patient 110.

As is conventional, an order handler module 112 of the prescription filler 102 processes the prescription(s) 104 for the patient 110 by submitting orders for the prescriptions 104 to the payor(s) associated with patient 110 (one of which is designated at reference numeral 114). The prescription(s) 104 approved by the payor 114 are sent to a fulfillment system 116 to prepare the prescription(s) 104 for delivery to the patient 110. Otherwise, the prescription(s) 104 are routed for manual handling and processing.

To estimate the costs of prescriptions (e.g., the estimated cost to purchase a quantity of medication prescribed), the prescription filler 102 includes a cost estimation module 118. The cost estimation module 118 may be, or include a portion of a memory unit (e.g., the program memory 602 of FIG. 6) configured to store software, and machine- or computer-readable instructions that, when executed by a processing unit (e.g., the processor 604 of FIG. 6), cause the cost estimation module 118 to estimate prescription costs in view of a patient's coverage(s), the medication and quantity prescribed, etc. In some examples, prescription costs are also estimated in view of ancillary information such as, but not limited to, demographic information, socioeconomic information, geographic information, etc.

In the illustrated example of FIG. 1, the cost estimation module 118 estimates prescription costs using a machine learning module 120. Prescription information (e.g., medication, quantity, prescription instruction(s), coverage information, ancillary information, etc.) are input to the machine learning module 120. The machine learning module 120 may be, or include a portion of a memory unit (e.g., the program memory 602 of FIG. 6) configured to store software, and machine- or computer-readable instructions that, when executed by a processing unit (e.g., the processor 604 of FIG. 6), cause the machine learning module 120 to executed a machine learning model to estimate prescription costs. In some examples, the machine learning module 120 implements gradient boosting machine learning, for example, using the open source eXtreme Gradient Boosting (XGBoost)) algorithm.

Figure 2:
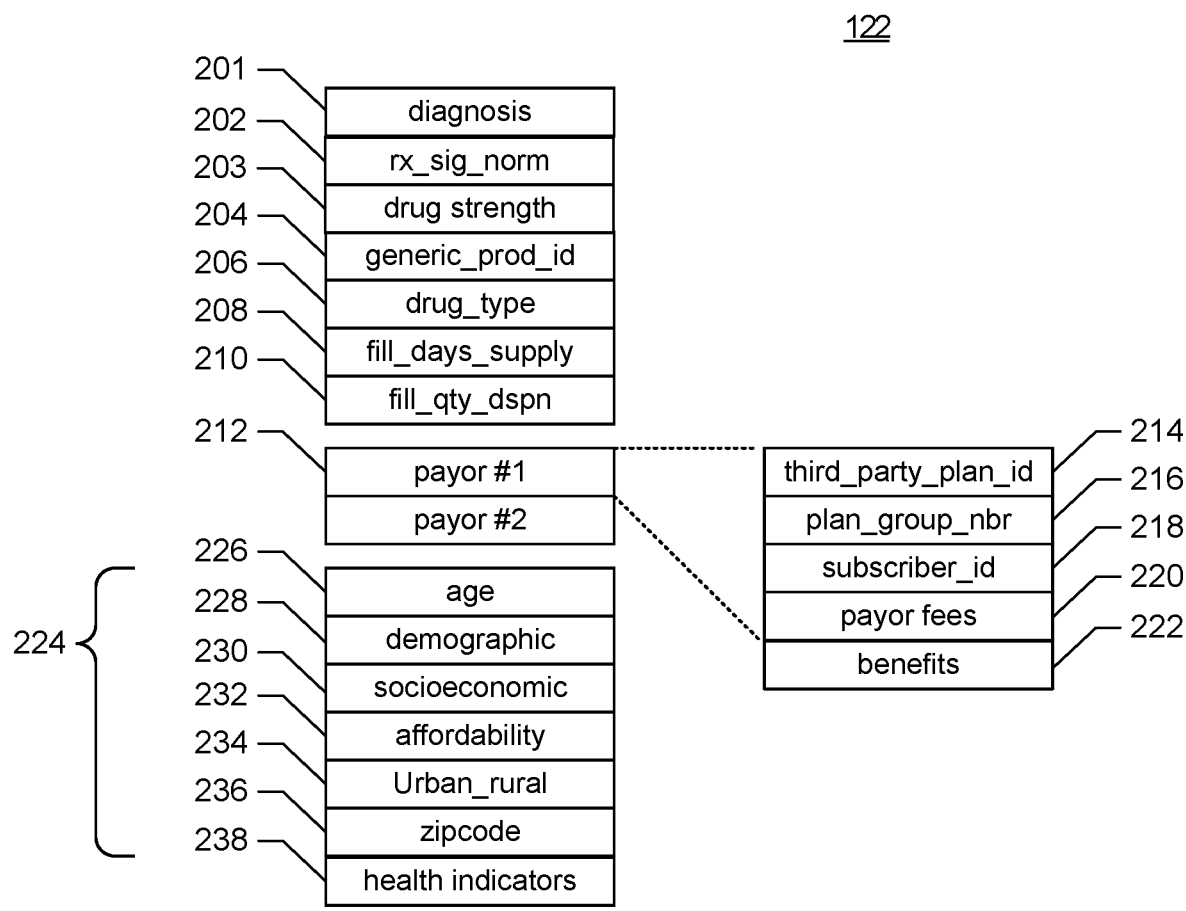
FIG. 2 is a block diagram of an example input vector for the machine learning module of FIG. 1.

An example input vector 122 to the machine learning module 120 is shown in FIG. 2. A diagnosis field 201 represents a medical diagnosis associated with the prescription. An rx_sign_norm field 202 represents usage information, i.e., how the medication is to be used (e.g., take 1 two times daily), a drug strength field 203 represents an amount of the medication per dose, a generic_prod_id field 204 provides information regarding generic equivalents, and a drug_type field 206 includes 14 characters that indicate drug group (e.g., decongestant), drug class (e.g., sympathomimetics), drug subclass (e.g., systemic decongestants), drug name (e.g., pseudoephedrine), drug name ext. (e.g., hydrochloride), dosage form (e.g., tablet) and strength (e.g., 60 mg). The input vector 122 further includes a fill_-days_supply field 208 that indicates how many days are being supplied, and a fill_qty_dspn field 210 that indicates how many are being dispensed. Payor information 212 for one or more payors includes a third_party_plan_id field 214 that represents the payor, a plan_group_nbr field 216 that identifies a patient's plan, and a subscriber_id field 218 that identifies an insured of the plan, fees associated with the payor are stored in a fees field 220, a benefits field 222 contains benefits information. In some examples, the input vector 122 includes ancillary information 224 such as an age field 226, a demographic field 228, a socioeconomic field 230, an affordability field 232, an urban/rural field 234, a zipcode field 236, and a health indicators field 238 (e.g., storing smoking information). While an example machine learning engine input vector 122 is shown in FIG. 2, the fields shown in FIG. 2 may be combined, divided, re-arranged, omitted, eliminated or implemented in any other way. Further, the input vector 122 may include one or more fields, entries, parameters, values in addition to, or instead of those illustrated in FIG. 2, or may include more than one of any or all of the illustrated fields, entries, parameters and values.

Returning to FIG. 1, the cost estimation module 118 estimates (e.g., determines, calculates, etc.) prescription costs in response to requests 124 for estimated costs. Requests 124 for estimated costs may be received from, for example, the prescriber 106 (or a representative thereof) via their laptop 108, from the patient 110 via a user device (e.g., a tablet 126), an employee of the prescription filler 102, etc. The cost estimation module 118 may also provide a proactive push notification of prescription costs based on events such as time of day, etc. to the requesting entity (e.g., the laptop 108 or the tablet 126).

When a request 124 for an estimated cost for a prescription 104 is received by the order handler module 112, the request 124 together with an input vector 122 corresponding to the prescription 104 is forwarded to the cost estimation module 118. The cost estimation module 118 passes the input vector 122 through the machine learning module 120, which estimates a cost 128 for the prescription 104. The estimated cost 128 is provided to the order handler module 112, which provides the estimated cost 128 to the requesting entity (e.g., the laptop 108 or the tablet 126), where it is presented electronically (e.g., on a screen), aurally (e.g., via telephone), via text message, etc. In some examples, a person receiving the estimated cost 128 can, in response, indicate whether they want to have the prescription 104 filled or refilled. In other examples, a person receiving the estimated cost 128, can be presented with why the estimated cost 128 increased for a prescription that they have gotten before, and be provided with options that can address this increase. In the case of the estimated cost 128 being received by the prescriber 106, the prescriber 106 can provide an alternative or substitute prescription when the patient 110 indicates the original prescription is too expensive. In this way, prescriptions that are more expensive than a patient can or is unwilling pay for are not unnecessarily filled. Moreover, alternative or substitute prescriptions can be made that ensure the patient 110 is receiving the medical care that they need or want. In some examples, when a cost estimate is requested, the order handler module 112 additionally identifies similar or alternative medication(s), and estimated associated cost(s) that a prescriber may consider. In some examples, information regarding overall compliance with picking up a particular medication can be provided (only 70% of prescriptions for this medication are picked up). In some examples, when ancillary information is included in the input vector 122, information regarding compliance for a group of persons including the patient's ancillary information can be provided (only 40% of people living in a particular neighborhood can afford this medication). Note that such information is aggregate statistical information and, thus, can be provided without exposing private information.

In some examples, the prescription filler 102 (e.g., the order handler module 112) implements a user interface (UI) (e.g., a web-based interface) that can be used to request and obtain estimated costs for prescriptions, and to request and obtain estimated cost(s) for alternative or similar medication(s).

In some examples, the cost estimation module 118 forms the input vector 122 based on the prescription 104. In some examples, the requests 124 for estimated costs 128 are routed through another portion or system of the prescription filler 102 outside conventional prescription processing.

The prescription filler 102, the laptop 108, the payor 114, and the tablet 126 may be communicatively coupled via any number or type(s) of communication network(s) 130. The communication network(s) include, but are not limited to, the Internet, a local area network (LAN), a metropolitan area network (MAN), a wide area network (WAN), a mobile, a wired network, a Wi-Fi® network, a cellular network, a wireless network, a private network, a virtual private network, etc.

Figure 6:
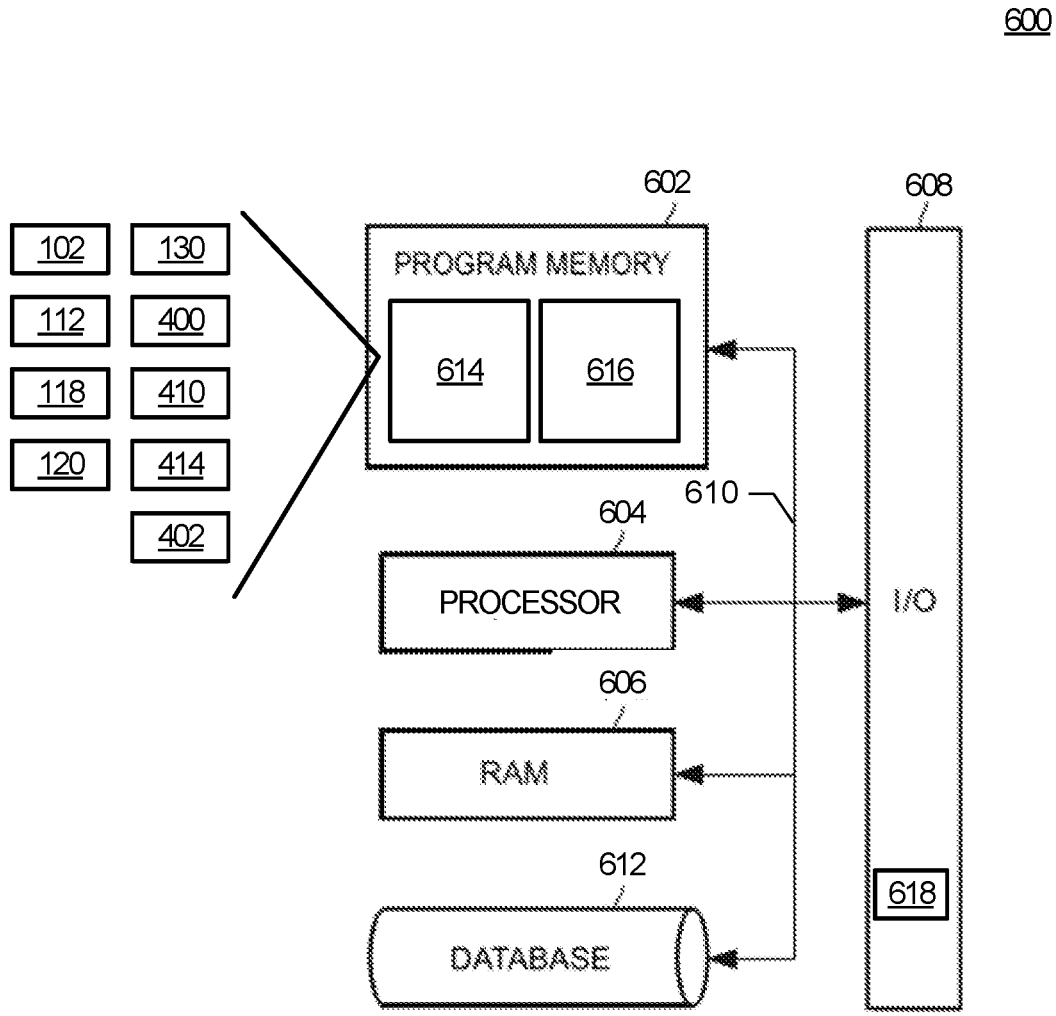
FIG. 6 is a block diagram of an example computing system that may be used to carry out the example processes of FIGS. 3 and 5, in accordance with the described embodiments.

While not shown for clarity of illustration, the prescription filler 102 of FIG. 1 may include various hardware components (e.g., a processor such as the processor 604 of FIG. 6, a server, a workstation, a distributed computing system, a graphics processing unit (GPU), a digital signal processor (DSP), etc.) that may execute software, and machine- or computer-readable instructions to estimate costs of prescriptions. The prescription filler 102 also includes data communication components for communicating between devices. Further, one or more of the elements, processes and devices illustrated in FIG. 1 may be combined, divided, re-arranged, omitted, eliminated or implemented in any other way. Further, the prescription filler 102 may include one or more elements, processes or devices in addition to, or instead of, those illustrated in FIG. 1, or may include more than one of any or all of the illustrated elements, processes and devices.

Figure 3:
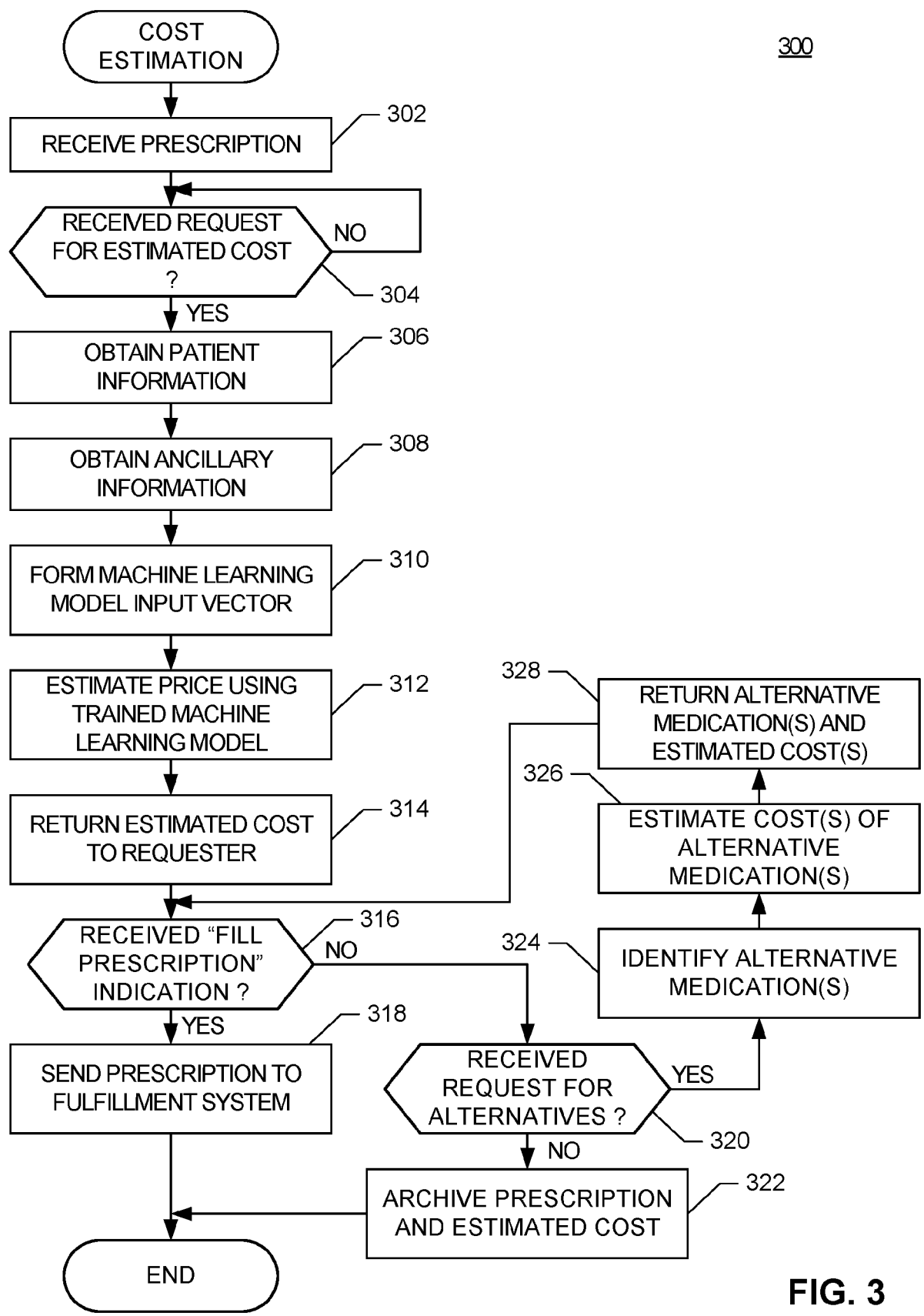
FIG. 3 is a flowchart representative of example method, hardware logic and instructions for implementing the prescription filler of FIG. 1.

A flowchart 300 representative of example processes, methods, software, firmware, and computer- or machine-readable instructions for implementing the prescription filler 102 is shown in FIG. 3. The processes, methods, software, and machine-readable or computer-readable instructions may be an executable program or portion of an executable program for execution by a processor such as the processor 604 of FIG. 6. The program may be embodied in software or instructions stored on a non-transitory computer- or machine-readable storage medium or disk associated with the processor 604. Further, although the example program is described with reference to the flowchart illustrated in FIG. 3, many other methods of implementing the prescription filler 102 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an application specific integrated circuit (ASIC), a programmable logic device (PLD), a field programmable gate array (FPGA), a field programmable logic device (FPLD), a logic circuit, etc.) structured to perform the corresponding operation without executing software or firmware.

The example process of FIG. 3 begins with the prescription filler 102 receiving a prescription 104 (block 302). If/when a request 124 for an estimated cost 128 is received for the prescription 104 from a requester (block 304), patient information is obtained comprising of demographics 224, payor 212, 214, 216, 218, 220 and 222 (block 306), and medication order information 201, 202, 203, 204, 206, 208 and 210. If used, ancillary information 224 is obtained (block 308). A machine learning input vector 122 is formed from the prescription 104 and the obtained information (block 310), and passed through the machine learning model implemented by the machine learning module 120 (block 312) to obtain a cost estimate 128 for the prescription 104. The cost estimate 128 is returned to the requester (block 314). If a "fill prescription" indication is received (block 316), the prescription 104 is filled by the fulfillment system 116 (block 318), and control exits from the example process of FIG. 3.

Returning to block 316, if a "fill prescription" indication is not received (block 316), and a request for alternatives is not received (block 320), the prescription 104 and estimated cost 128 are stored for subsequent retrieval (block 322), and control exits from the example process of FIG. 3.

Returning to block 320, if a request for alternatives is received (block 320), one or more alternative or similar medications are identified (block 324), and costs for the one or more alternative medications are estimated (block 326). The one or more alternative or similar medications and their estimated costs are returned to the requester (block 328), and control returns to block 316.

Figure 4:
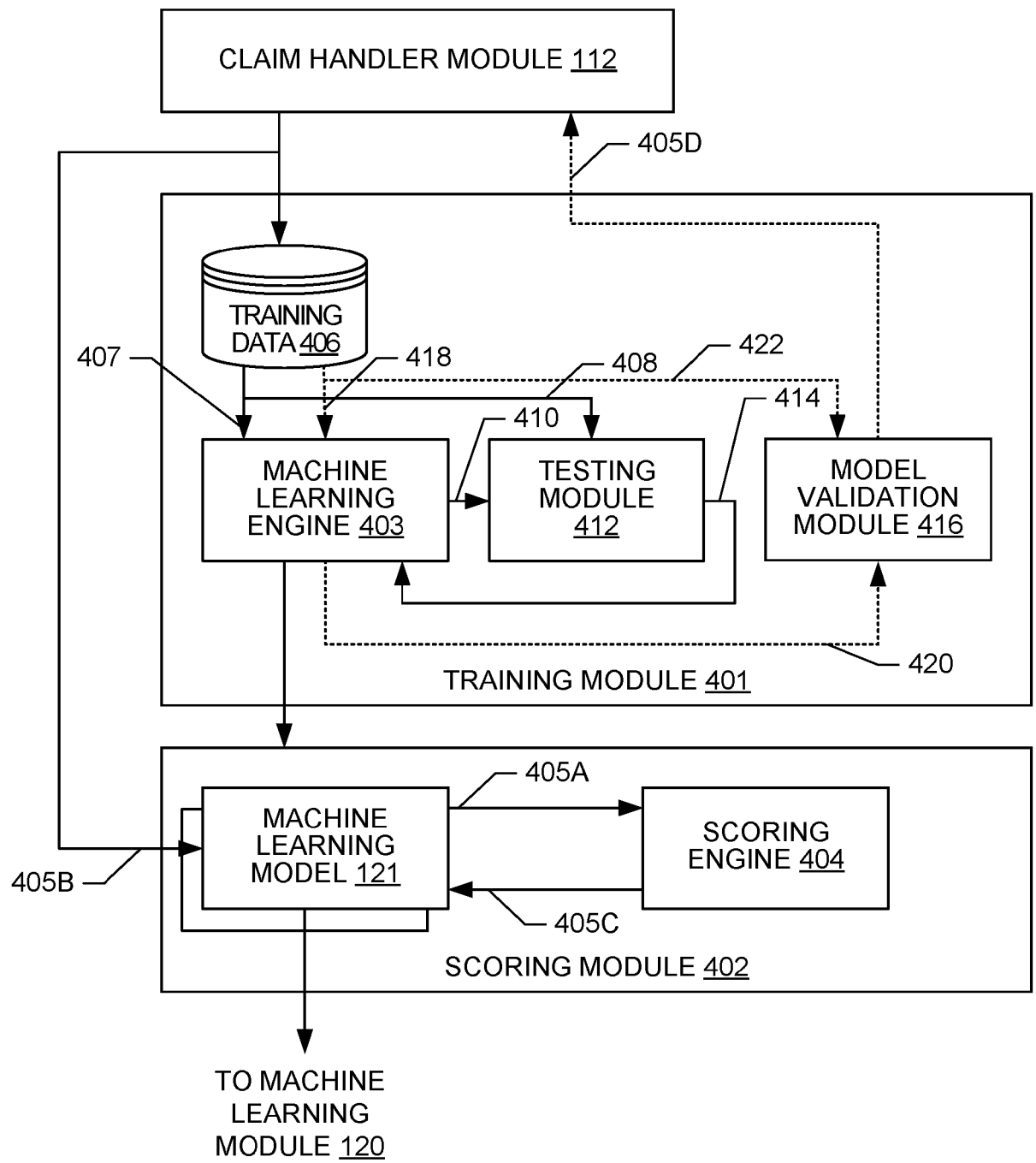
FIG. 4 is a block diagram of an example machine learning training module to train the machine learning module of FIG. 1, in accordance with teachings of this disclosure.

FIG. 4 is a block diagram of an example machine learning training module 400 having a training module 401 and a scoring module 402. The training module 401 includes a machine learning engine 403 for training a machine learning module. The scoring module 402 scores a final machine leaning model 121. Both the training module 401 and the scoring module 402 can be executed for use as the machine learning module 120 of FIG. 1. There can be one or more machine learning models 121 for scoring within the scoring module 402. The training module 401 and the scoring module 402 may be, or include a portion of a memory unit (e.g., the program memory 602 of FIG. 6) configured to store software, and machine- or computer-readable instructions that, when executed by a processing unit (e.g., the processor 604 of FIG. 6), cause the training module 401 to train, test and validate a machine learning model 121 from the machine learning engine 403, and cause the scoring module 402 to provide the cost estimates to the scoring engine 404 or the requesting entity (e.g., the laptop 108 or the tablet 126). The scoring engine 404 is used to simulate the requesting entity using API messaging such as RESTful API requests 405A to simulate requests 405B for cost, and RESTful API responses 405C to simulate the delivery 405D of cost estimates 128. The scoring module 402 is used to facilitate this messaging and manage the machine learning model 121 such that the machine learning training module 400 can operate within the system 100.

The machine learning training module 400 includes a database of training data 406 that stores prescriptions 407, and prices 408 at which the prescriptions 407 were sold on any number or type(s) of non-transitory computer- or machine-readable storage medium or disk using any number or type(s) of data structures.

As used herein, a non-transitory computer- or machine-readable storage medium or disk may be, but is not limited to, one or more of a hard disk drive (HDD), an optical storage drive, a solid-state storage device, a solid-state drive (SSD), a read-only memory (ROM), a random-access memory (RAM), a compact disc (CD), a compact disc read-only memory (CD-ROM), a digital versatile disk (DVD), a Blu-ray disk, a cache, a flash memory, or any other storage device or storage disk in which information may be stored for any duration (e.g., permanently, for an extended time period, for a brief instance, for temporarily buffering, for caching of the information, etc.).

Input vectors 122 are formed for the prescriptions 407 and passed through the machine learning engine 403 to form trial estimated costs 410. In the illustrated example of FIG. 4, the developing machine learning model within the machine learning engine 403 is trained using supervised learning. Accordingly, a testing module 412, which may be, or include a portion of a memory unit (e.g., the program memory 602 of FIG. 6) configured to store software, and machine- or computer-readable instructions that, when executed by a processing unit (e.g., the processor 604 of FIG. 6), cause the testing module 412 to compare the trial estimated costs 410 determined by the machine learning engine 403 for the prescriptions 406 with the actual sold prices 408 for the prescriptions 407 to form errors 414 that are used to develop and update the machine learning engine 403. The machine learning engine 403 develops, deploys and updates the final machine learning model 121 using, for example, gradient boosting machine learning, for example, using the open source eXtreme Gradient Boosting (XGBoost)) algorithm, a neural network, deep learning, a regression technique, etc.

To validate the developing machine learning model within the machine learning engine 403, the training module 401 includes a model validation module 416. The model validation module 416 may be, or include a portion of a memory unit (e.g., the program memory 602 of FIG. 6) configured to store software, and machine- or computer-readable instructions that, when executed by a processing unit (e.g., the processor 604 of FIG. 6), cause the model validation module 416 to statistically validate the developing machine learning model using k-fold cross-validation. The data 406 is randomly split into k parts. The developing machine learning model is trained using k-1 of the k parts of the data 406 to form the prescriptions 407. The machine learning module 120 is evaluated using the remaining 1 (one) part of the data 406 to form prescriptions 418, which the machine learning engine 403 has not been exposed to. Outputs 420 of the developing machine learning model for the prescriptions 418 are compared to actual sold prices 422 for the prescriptions 418 by the model validation module 416 to determine the performance or convergence of developing machine learning model. Performance or convergence can be determined by, for example, identifying when a metric computer over the errors 414 (e.g., a mean-square metric, a rate-of-decrease metric, etc.) satisfies a criteria (e.g., a metric is less than a predetermined threshold, such as a root mean squared error).

In some examples, the developing machine learning model within the machine learning engine 403 is initially trained using historical prescription and sold price data. The machine learning engine 403 may then deploy one or more new or updated machine learning models as new prescriptions are sold. For example, deploying a machine learning model 121 running in parallel with the machine learning engine 403 can used to estimate costs for live prescription cost estimate requests. Periodically or aperiodically, the machine learning model 121 can be updated from the parallel machine learning engine 403. In addition, for example, the machine learning model 121 can be deployed as one or more MLeap model formats to perform scoring within the scoring module 402 and can provide these cost estimates 128 in the form of predictions. MLeap is an open source serialization format and execution engine for machine learning pipelines, The MLeap format enables productionalization and scaling on a Docker container, Kubernetes cluster or similar. Similarly, predictions could be recorded and compared with post-training results to improve cost estimate prediction. Other deployable model formats may include PMML, Onyx, PFA, pickle, etc.

Figure 5:
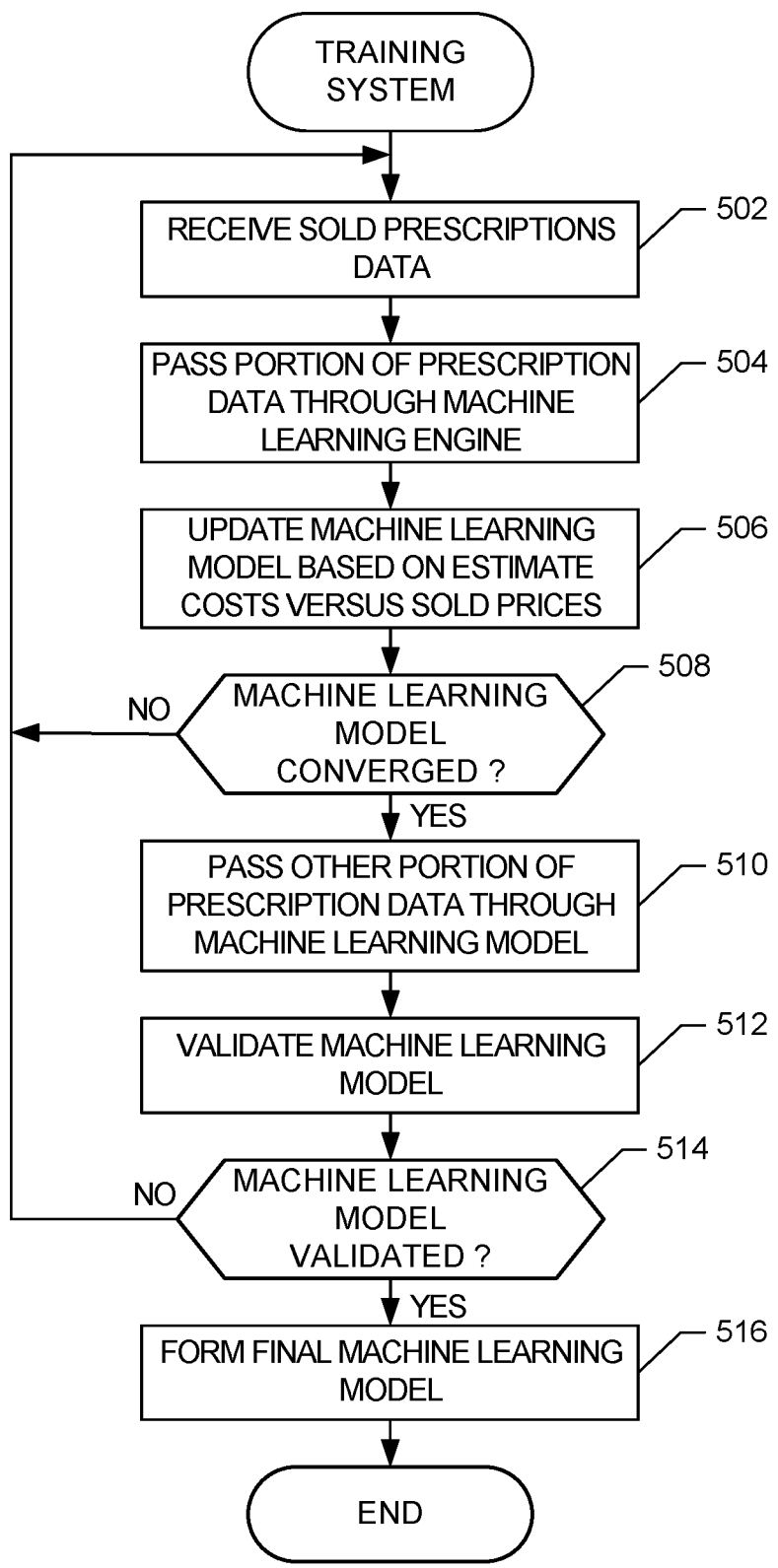
FIG. 5 is a flowchart representative of example method, hardware logic and instructions for training the machine learning model of FIG. 1.

A flowchart 500 representative of example processes, methods, software, firmware, and computer- or machine-readable instructions for implementing the machine learning training module 400 is shown in FIG. 5. The processes, methods, software and instructions may be an executable program or portion of an executable program for execution by a processor such as the processor 604 of FIG. 6. The program may be embodied in software or instructions stored on a non-transitory computer- or machine-readable storage medium or disk associated with the processor 604. Further, although the example program is described with reference to the flowchart illustrated in FIG. 5, many other methods of implementing the example machine learning training module 400 may alternatively be used. For example, the order of execution of the blocks may be changed, and/or some of the blocks described may be changed, eliminated, or combined. Additionally, or alternatively, any or all of the blocks may be implemented by one or more hardware circuits (e.g., discrete and/or integrated analog and/or digital circuitry, an ASIC, a PLD, an FPGA, an FPLD, a logic circuit, etc.) structured to perform the corresponding operation without executing software or firmware.

The example process of FIG. 5 begins with receiving prescriptions and storing them in the training data database 406 (block 502). Prescriptions 407 of the k-1 of k portions of the data 406 are passed through the machine learning engine 403 (block 504), and the developing machine learning model within the machine learning engine 403 is updated based on comparisons by the testing module 412 of the outputs 410 of the developing machine learning model and sold prices for the prescriptions 407 of the k-1 portions of the data 406 (block 506). If training of the developing machine learning model has not converged (block 508), control returns to block 504 to continue training the developing machine learning model. If training of the developing machine learning model has converged (block 508), the prescriptions 418 of the remaining portion of the data 406 are passed through the machine learning engine 403 (block 510), and outputs 420 of the developing machine learning model are used by the model validation module 416 to validate the developing machine learning model (block 512). If the developing machine learning model validates (block 514), the machine learning engine 403 is used to form the final machine learning model 121 (block 516) (e.g., coefficients are copied, etc.), and control exits from the example process of FIG. 5. Otherwise, if the developing machine learning model does not validate (block 514), then control returns to block 502 to continue training.

Referring now to FIG. 6, a block diagram of an example computing system 600 to estimate prescription costs in accordance with described embodiments is shown. The example computing system 600 may be used to, for example, implement the prescription filler 102, the order handler module 112, the cost estimation module 118, the machine learning module 120, and the UI 130. The computing system 600 may also be used to, for example, implement the machine learning training module 400, the training module 401, the scoring module 402, the machine learning engine 403, the testing module 412, the model validation module 416, and the scoring engine 404.

The computing system 600 includes a program memory 602, a processor 604, a RAM 606, and an I/O circuit 608, all of which are interconnected via an address/data bus 610. The program memory 602 may store software, and machine- or computer-readable instructions, which may be executed by the processor 604.

It should be appreciated that although FIG. 6 depicts only one processor 604, the computing system 600 may include multiple processors 604. Example processors 604 include a programmable processor, a programmable controller, a GPU, a DSP, an ASIC, a PLD, an FPGA, an FPLD, etc.

Similarly, the program memory 602 may include memories, for example, one or more RAMs (e.g., a RAM 614) or one or more program memories (e.g., a ROM 616), or a cache (not shown) storing one or more corresponding software, and machine- or computer-instructions. For example, the program memory 602 stores software, and machine- or computer-readable instructions, or computer-executable instructions that may be executed by the processor 604 to implement the prescription filler 102, the order handler module 112, the cost estimation module 118, the machine learning module 120, and the UI 130; and may also be used to implement the machine learning training module 400, the training module 401, the scoring module 402, the machine learning engine 403, the testing module 412, the model validation module 416, and the scoring engine 404 to estimate prescription costs. The software, machine-readable instructions, or computer-executable instructions may be stored on separate non-transitory computer- or machine-readable storage mediums or disks, or at different physical locations.

In some embodiments, the processor 604 may also include, or otherwise be communicatively connected to, a database 612 or other data storage mechanism (one or more hard disk drives, optical storage drives, solid state storage devices, CDs, CD-ROMs, DVDs, Blu-ray disks, etc.). In some examples, the database 612 stores the training data database 406.

Although FIG. 6 depicts the I/O circuit 608 as a single block, the I/O circuit 608 may include a number of different types of I/O circuits or components that enable the processor 604 to communicate with peripheral I/O devices. The peripheral I/O devices may be any desired type of I/O device such as a keyboard, a display (a liquid crystal display (LCD), a cathode ray tube (CRT) display, touch, etc.), a navigation device (a mouse, a trackball, a capacitive touch pad, a joystick, etc.), speaker, a microphone, a button, a communication interface, an antenna, etc.

The I/O circuit 608 may include a number of different network transceivers 618 that enable the computing system 600 to communicate with another computer system via, e.g., a network (e.g., the communication network 130). The network transceiver 618 may be a Wi-Fi transceiver, a Bluetooth transceiver, an infrared transceiver, a cellular transceiver, an Ethernet network transceiver, an asynchronous transfer mode (ATM) network transceiver, a digital subscriber line (DSL) modem, a cable modem, etc.

The program memory 602, the RAM(s) 606, 614 and the ROM(s) 616 may be implemented in any known form of volatile or non-volatile computer storage media, including but not limited to, semiconductor memories, magnetically readable memories, and/or optically readable memories, for example, but does not include carrier waves.

Example methods, apparatus, and articles of manufacture to estimate prescription costs are disclosed herein. Further examples and combinations thereof include at least the following. A computer-implemented method, executed by a processor, to estimate a cost of a prescription for a medication.

Example 1 is a computer-implemented method, executed by a processor, to estimate a cost of a prescription for a medication, the method includes receiving, with a processor, a prescription for a medication for a patient, receiving, with the processor from an entity, a request for an estimated cost for the prescription, processing, with a machine learning model, the prescription to determine the estimated cost of the medication for the patient, and providing, with the processor, the estimated cost to the entity.

Example 2 is the method of example 1, wherein the entity is a person.

Example 3 is the method of example 2, wherein the prescription is received from the patient.

Example 4 is the method of any of examples 1 or 3, wherein the entity is a prescriber for the prescription, or a representative of the prescriber.

Example 5 is the method of example 4, further comprising providing, with the processor, an alternative medication and estimated cost for the alternative medication to the entity.

Example 6 is the method of example 4, wherein the prescription and the request are received, and the estimated cost is provided while the patient is in a vicinity of the prescriber, or the representative of the prescriber.

Example 7 is the method of example 6, further comprising receiving, in response to the providing of the estimated cost, an indication to fulfill the prescription, or an alternative medication for the patient.

Example 8 is the method of any of examples 1 to 7, further comprising receiving, with the processor, an indication of whether to fulfill the prescription in response to the providing of the estimated cost.

Example 9 is the method of any of examples 1 to 8, wherein processing, with the machine learning model, the prescription includes inputting to the machine learning model at least one of medication information, usage information, payor information, demographic information, socioeconomic information, or geographic information.

Example 10 is the method of any of examples 1 to 9, further comprising training the machine learning model with data representing a plurality of sold prescriptions, each sold prescription including prescription information and an actual sold cost.

Example 11 is the method of example 10, wherein training the machine learning model includes applying gradient boosting.

Example 12 is the method of example 10, further comprising training the machine learning model with a first portion of the data, and validate the machine learning model with a second portion of the data.

Example 13 is the method of any of examples 1 to 12, further comprising providing information representing a likelihood the medication will be picked up.

Example 14 is a non-transitory computer-readable storage medium storing instructions that, when executed, cause a machine to receive a prescription for a medication for a patient, receive, from an entity, a request for an estimated cost for the prescription, process the prescription with a machine learning model to determine the estimated cost of the medication for the patient, and provide the estimated cost to the entity.

Example 15 is the non-transitory computer-readable storage medium of example 14, wherein the entity is a person.

Example 16 is the non-transitory computer-readable storage medium of example 14 or 15, wherein the entity is a prescriber for the prescription, or a representative of the prescriber, and further including instructions that, when executed, cause the machine to provide an alternative medication and estimated cost for the alternative medication to the entity, provide information representing a likelihood the medication will be picked up, and fill the prescription when an indication to fulfill the prescription is received in response to at least one of the estimated cost, the alternative medication, of the likelihood.

Example 17 is the non-transitory computer-readable storage medium of any of examples 14 to 16, wherein processing the prescription with the machine learning model includes inputting to the machine learning model at least one of medication information, usage information, payor, demographic information, socioeconomic information, or geographic information.

Example 18 is the non-transitory computer-readable storage medium of any of examples 14 to 17, including further instructions that, when executed, cause the machine to train the machine learning model with data representing a plurality of sold prescriptions, each sold prescription including prescription information and an actual sold cost.

Example 19 is the non-transitory computer-readable storage medium of example 18, wherein training the machine learning model includes applying gradient boosting.

Example 20 is the non-transitory computer-readable storage medium of example 18, including further instructions that, when executed, cause the machine to train the machine learning model with a first portion of the data, and validate training of the machine learning model using a second portion of the data is used to validate.

Some examples may be described using "coupled" or "connected" along with their derivatives. For example, some examples may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

Unless specifically stated otherwise, "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

As used herein, the terms "comprises," "comprising," "includes," "including," "has," "having" or any other variation thereof, are intended to cover a non-exclusive inclusion. Thus, whenever a claim employs any form of "include" or "comprise" (e.g., comprises, includes, comprising, including, having, etc.) as a preamble or within a claim recitation of any kind, it is to be understood that additional elements, terms, etc. may be present without falling outside the scope of the corresponding claim or recitation. As used herein, when the phrase "at least" is used as the transition term in, for example, a preamble of a claim, it is open-ended in the same manner as the term "comprising" and "including" are open ended.

Further, unless expressly stated to the contrary, "or" refers to an inclusive or and not to an exclusive or. For example, A, B or C refers to any combination or subset of A, B, C such as (1) A alone, (2) B alone, (3) C alone, (4) A with B, (5) A with C, (6) B with C, and (7) A with B and with C. As used herein, the phrase "at least one of A and B" is intended to refer to implementations including any of (1) at least one A, (2) at least one B, and (3) at least one A and at least one B. Similarly, the phrase "at least one of A or B" is intended to refer to implementations including any of (1) at least one A, (2) at least one B, and (3) at least one A and at least one B.

As used herein, the expressions "in communication," "coupled" and "connected, including variations thereof, encompasses direct communication and/or indirect communication through one or more intermediary components, and does not require direct physical (e.g., wired) communication and/or constant communication, but rather additionally includes selective communication at periodic intervals, scheduled intervals, aperiodic intervals, and/or one-time events.

As used herein, the term non-transitory computer-readable medium is expressly defined to include any type of computer-readable storage device and/or storage disk and to exclude propagating signals and to exclude transmission media. As used herein, the term non-transitory machine-readable medium is expressly defined to include any type of machine-readable storage device and/or storage disk and to exclude propagating signals and to exclude transmission media.

Any references, including publications, patent applications, and patents cited herein are hereby incorporated in their entirety by reference to the same extent as if each reference were individually and specifically indicated to be incorporated by reference and were set forth in its entirety herein.

Finally, unless a claim element is defined by reciting the word "means" and a function without the recital of any structure, it is not intended that the scope of any claim element be interpreted based on the application of 35 U.S.C. § 112, sixth paragraph.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A computer-implemented method, executed by one or more processors, to estimate a cost of a prescription for a medication, the method comprising:
   receiving a prescription for a medication for a patient;
   receiving a request for an estimated cost for the prescription for the patient from an entity;
   forming an input vector including prescription information for the received prescription, and payor information for the patient;
   processing the input vector for the received prescription, with a trained machine learning model, to determine the estimated cost of the medication for the patient, wherein the machine learning model is trained until it converges with data representing a plurality of sold prescriptions by updating the machine learning model based upon computed differences between (i) predicted costs determined by the machine learning model based on prescription information for the plurality of sold prescriptions and payor information, and (ii) actual sold costs for the plurality of sold prescriptions;
   providing the estimated cost to the entity; and
   deploying the updated machine learning model.

2. The method of claim 1, wherein the entity is a person.

3. The method of claim 2, wherein the prescription is received from the patient.

4. The method of claim 1, wherein the entity is a prescriber for the prescription, or a representative of the prescriber.

5. The method of claim 4, further comprising providing an alternative medication and estimated cost for the alternative medication to the entity.

6. The method of claim 4, wherein the prescription and the request are received, and the estimated cost is provided while the patient is in a vicinity of the prescriber, or the representative of the prescriber.

7. The method of claim 6, further comprising when, in response to the providing of the estimated cost, an indication to fulfill the prescription, or an alternative medication for the patient is received, cause the prescription or the alternative medication to be filled for delivery to the patient.

8. The method of claim 1, wherein the input vector further includes one or more of demographic information, socioeconomic information, or geographic information.

9. The method of claim 1, wherein the machine learning model is updated by applying gradient boosting.

10. The method of claim 1, wherein the machine learning model is validated with second data representing a second plurality of sold prescriptions, the second data including for each sold prescription: (i) prescription information, (ii) payor information, and (iii) an actual sold cost.

11. The method of claim 1, further comprising providing to the entity information representing a likelihood that the medication will be picked up by the patient.

12. The method of claim 1, wherein the machine learning model is converged when a metric computed over one or more of the differences satisfies a criteria.

13. A non-transitory computer-readable storage medium storing computer-readable instructions that, when executed by one or more processors, cause a machine to:
receive a prescription for a medication for a patient;
receive, from an entity, a request for an estimated cost for the prescription for the patient;
form an input vector including prescription information for the received prescription, and payor information for the patient;
process the input vector with a trained machine learning model to determine the estimated cost of the medication for the patient, wherein the machine learning model is trained until it converges with data representing a plurality of sold prescriptions by updating the machine learning model based upon computed differences between (i) predicted costs determined by the machine learning model based on prescription information for the plurality of sold prescriptions and payor information, and (ii) actual sold costs for the plurality of sold prescriptions;
provide the estimated cost to the entity; and
deploy the updated machine learning model.

14. The non-transitory computer-readable storage medium of claim 13, wherein the entity is a person.

15. The non-transitory computer-readable storage medium of claim 13, wherein the entity is a prescriber for the prescription, or a representative of the prescriber, and wherein the instructions, when executed by the one or more processors, cause the machine to:
provide an alternative medication and estimated cost for the alternative medication to the entity;
provide information representing a likelihood that the medication will be picked up by the patient; and
cause the prescription to be filled when an indication to fulfill the prescription is received in response to at least one of the estimated cost, the alternative medication, of the likelihood.

16. The non-transitory computer-readable storage medium of claim 13, wherein the input vector further includes one or more of demographic information, socioeconomic information, or geographic information.

17. The non-transitory computer-readable storage medium of claim 13, wherein the machine learning model is updated using gradient boosting.

18. The non-transitory computer-readable storage medium of claim 13, wherein the machine learning model is validated with second data representing a second plurality of sold prescriptions, the second data including for each sold prescription: (i) prescription information, (ii) payor information, and (iii) an actual sold cost.

19. The non-transitory computer-readable storage medium of claim 13, wherein the machine learning model is converged when a metric computed over one or more of the differences satisfies a criteria.

20. A computer-implemented method, executed by one or more processors, to train a machine learning model for estimating costs of prescriptions, the method comprising:
obtaining data representing a plurality of sold prescriptions, the data including for each sold prescription: (i) prescription information, (ii) payor information, and (iii) an actual sold cost;
for each sold prescription of the plurality of sold prescriptions until the machine learning model converges:
forming an input vector for the sold prescription that includes the prescription information and the payor information for the sold prescription,
processing the input vector for the sold prescription with the machine learning model to generate an estimated cost for the sold prescription,
determining a difference between the estimated cost for the sold prescription and the actual sold cost for the sold prescription, and
updating the machine learning model based on the difference; and
when the machine learning model converges, deploying, on one or more processors, the updated trained machine learning model for use in estimating costs of prescriptions for medications.

21. The method of claim 20, further comprising:
obtaining second data representing a second plurality of sold prescriptions, the second data including for each sold prescription of the second plurality of sold prescriptions: (i) prescription information, (ii) payor information, and (iii) an actual sold cost;
for each sold prescription of the second plurality of sold prescriptions:
forming an input vector for the sold prescription that includes the prescription information and the payor information for the sold prescription,
processing the input vector with the trained machine learning model to generate an estimated cost for the sold prescription, and
determining a difference between the estimated cost for the sold prescription and the actual sold cost for the sold prescription;
computing a statistical metric of the differences for the second plurality of sold prescriptions; and
determining whether the training of the machine learning model has converged based on the statistical metric.

22. The method of claim 20, wherein updating the machine learning model includes applying gradient boosting.

23. The method of claim 20,
wherein the prescription information includes one or more of a medical diagnosis, drug usage information, a drug name, a drug strength, a drug amount, a drug type, a drug class, a drug subclass, or a drug form, and
wherein the payor information includes one or more of a payor identifier, a plan group identifier, a subscriber identifier, fees information, or benefits information.

24. The method of claim 20, further comprising:
receiving a prescription for a medication for a patient;
receiving a request for an estimated cost for the prescription for the patient;
forming an input vector including prescription information for the received prescription, and payor information for the patient;
processing the input vector for the received prescription, with the trained machine learning model, to determine the estimated cost of the medication for the patient;
obtaining an actual cost of the medication for the patient; and
updating the machine learning model based upon a difference between the estimated cost of the medication for the patient and the actual cost of the medication for the patient.

* * * * *